United States Patent
Chojecki et al.

(10) Patent No.: US 11,986,799 B2
(45) Date of Patent: May 21, 2024

(54) CATALYSTS COMPRISING A ZIRCONIA AND GALLIUM OXIDE COMPONENT FOR PRODUCTION OF $C_2$ TO $C_4$ OLEFINS

(71) Applicant: Dow Global Technologies LLC, Midland, MI (US)

(72) Inventors: Adam Chojecki, Ghent (BE); Alexey Kirilin, Terneuzen (NL); Andrzej Malek, Midland, MI (US); Joseph F. DeWilde, Midland, MI (US); Vera P. Santos Castro, Terneuzen (NL); David F. Yancey, Midland, MI (US); Kyle C. Andrews, Midland, MI (US)

(73) Assignee: Dow Global Technologies LLLC, Midland, MI (US)

( * ) Notice: Subject to any disclaimer, the term of this patent is extended or adjusted under 35 U.S.C. 154(b) by 414 days.

(21) Appl. No.: 17/417,846

(22) PCT Filed: Dec. 16, 2019

(86) PCT No.: PCT/US2019/066526
§ 371 (c)(1),
(2) Date: Jun. 24, 2021

(87) PCT Pub. No.: WO2020/139599
PCT Pub. Date: Jul. 2, 2020

(65) Prior Publication Data
US 2022/0080392 A1 Mar. 17, 2022

Related U.S. Application Data

(60) Provisional application No. 62/785,828, filed on Dec. 28, 2018.

(51) Int. Cl.

| | | |
|---|---|---|
| *B01J 23/08* | (2006.01) |
| *B01J 23/00* | (2006.01) |
| *B01J 29/85* | (2006.01) |
| *B01J 35/00* | (2006.01) |
| *B01J 35/61* | (2024.01) |
| *B01J 37/02* | (2006.01) |
| *B01J 37/04* | (2006.01) |
| *C07C 1/04* | (2006.01) |

(52) U.S. Cl.
CPC ............ *B01J 23/08* (2013.01); *B01J 23/002* (2013.01); *B01J 29/85* (2013.01); *B01J 35/19* (2024.01); *B01J 35/612* (2024.01); *B01J 35/613* (2024.01); *B01J 35/615* (2024.01); *B01J 37/0201* (2013.01); *B01J 37/04* (2013.01); *C07C 1/043* (2013.01); *C07C 2521/06* (2013.01); *C07C 2523/08* (2013.01); *C07C 2529/85* (2013.01)

(58) Field of Classification Search
CPC ......... C07C 11/08; C07C 11/04; C07C 11/06; C07C 2529/85; C07C 2523/08; C07C 2521/06; B01J 23/08; B01J 29/85; B01J 35/1019

See application file for complete search history.

(56) References Cited

U.S. PATENT DOCUMENTS 11,084,026 B2 * 8/2021 Pan .......................... B01J 21/04
2014/0113981 A1 4/2014 Yilmaz et al.

FOREIGN PATENT DOCUMENTS

| CN | 1065026 A | 10/1992 |
|---|---|---|
| CN | 103071528 A | 5/2013 |
| CN | 104307560 A | 1/2015 |
| CN | 105396571 A | 3/2016 |
| CN | 106607078 A | 5/2017 |
| CN | 106694028 A | 5/2017 |
| CN | 110180549 A | 8/2019 |
| CN | 110227539 A | 9/2019 |
| EP | 0070690 A1 | 1/1983 |
| JP | 2017088597 A | 5/2017 |
| WO | 03089392 A1 | 10/2003 |
| WO | 2010068364 A2 | 6/2010 |
| WO | 2012000883 A1 | 1/2012 |
| WO | 2017074558 A1 | 5/2017 |
| WO | 2017118572 A1 | 7/2017 |
| WO | 2018119195 A1 | 6/2018 |

OTHER PUBLICATIONS

Freeman, Methanol to Hydrocarbons: Enhanced Aromatic Formation Using Composite Group 13 Oxide/H-ZSM-5 Catalysts, Catalysis Letters, 82 (2002) 217.
Freeman, Methanol to hydrocarbons: enhanced aromatic formation using a composite GaO—H—ZSM-5 catalyst, Chemical Communications, (2001) 1754.
(Continued)

*Primary Examiner* — Jafar F Parsa
(74) *Attorney, Agent, or Firm* — Dinsmore & Shohl LLP

(57) ABSTRACT

A process for preparing $C_2$ to $C_4$ olefins includes introducing a feed stream comprising hydrogen gas and a carbon-containing gas selected from carbon monoxide, carbon dioxide, and mixtures thereof into a reaction zone of a reactor. The feed stream is converted into a product stream including $C_2$ to $C_4$ olefins in the reaction zone in the presence of the hybrid catalyst. The hybrid catalyst includes a metal oxide catalyst component comprising gallium oxide and phase pure zirconia, and a microporous catalyst component.

18 Claims, No Drawings

(56) References Cited

OTHER PUBLICATIONS

Inui, Effective synthesis of ethanol from CO2 on polyfunctional composite catalysts, Catalysis Today, 45 (1998) 209.

Martin, Indium Oxide as a Superior Catalyst for Methanol Synthesis by CO2 Hydrogenation, Angewandte Chemie International Edition, 55 (2016) 6261.

Inui, Structure and function of Cu-based composite catalysts for highly effective synthesis of methanol by hydrogenation of CO2 and CO, Catalysis Today, 36 (1997) 25.

Sanguineti, Copper-gallia interaction in Cu—Ga2O3—ZrO2 catalysts for methanol production from carbon oxide(s) hydrogenation, Applied Catalysis A: General, 2015, vol. 504, 476.

Saito, Development of copper/zinc oxide-based multicomponent catalysts for methanol synthesis from carbon dioxide and hydrogen, Applied Catalysis A: General, 1996, vol. 138, 311.

Saito, Development of Cu/ZnO-based high performance catalysts for methanol synthesis by CO2 hydrogenation, Energy Conversion and Management, 1995, vol. 36, 577.

Fujitani, Development of an active Ga2O3 supported palladium catalyst for the synthesis of methanol from carbon dioxide and hydrogen, Applied Catalysis A: General, 1995, vol. 125, L199.

Garcia-Trenco Pd2Ga-Based Colloids as Highly Active Catalysts for the Hydrogenation of CO2 to Methanol, ACS Catalysis, 2017, vol. 7, 1186.

Collins, Hydrogen Spillover in Ga2O3—Pd/SiO2 Catalysts for Methanol Synthesis from CO2/H2, Catalysis Letters, 2005, vol. 103, 83.

Ihm, CO2 Hydrogenation over Copper-Based Hybrid Catalysts for the Synthesis of Oxygenates, in: Utilization of Greenhouse Gases, American Chemical Society, 2003, pp. 183.

CN Office Action dated Jun. 7, 2023, pertaining to CN Patent Application No. 201980090309.5, 11 pgs.

Su et al. "Direct Conversion of Syngas into Light Olefins over Zirconium-Doped Indium(III) Oxide and SAPO-34 Bifunctional Catalysts: Design of Oxide Component and Construction of Reaction Network", ChemCatChem 2018, 10, pp. 1536-1541.

International Search Report and Written Opinion pertaining to PCT/US2019/066526, dated Mar. 16, 2020.

Cheng et al., "Direct and Highly Selective Conversion of Synthesis Gas into Lower Olefins: Design of a Bifunctional Catalyst Combining Methanol Synthesis and Carbon-Carbon Coupling", Angewadnte Chemie, 2016, 55/16, 4725-4728.

Liu et al., "Selective transformation of carbon dioxide into lower olefins with a bifunctional catalyst composed of ZnGa2O4 and SAPO-34", Chemical Communications, 2018, 54, 140.

Arai et al., "Selective Formation of Ethene from CO Hydrogenation Reaction over In2O3—CeO2, —La2O3, and —Y2O3 Mixed Oxide Catalysts", Bulletin of the Chemical Society of Japan, 1989, 2, 349.

Tan et al., "Syntheses of Isobutane and Branched Higher Hydrocarbons from Carbon Dioxide and Hydrogen over Composite Catalysts", Industrial & Engineering Chemistry Research, 1999, 38, 3225.

Brazil Office Action dated Sep. 8, 2023, pertaining to BR Patent Application No. BR112021012703.8, 8 pgs.

Chinese Office Action dated Dec. 25, 2023, pertaining CN Patent Application No. 2019800903095, 8 pgs.

\* cited by examiner

CATALYSTS COMPRISING A ZIRCONIA AND GALLIUM OXIDE COMPONENT FOR PRODUCTION OF $C_2$ TO $C_4$ OLEFINS

CROSS-REFERENCE TO RELATED APPLICATIONS

This application is a National Stage Entry under 35 U.S.C. § 371 of International Patent Application No. PCT/US2019/066526, filed Dec. 16, 2019, which claims priority to U.S. Provisional Patent Application No. 62/785,828 filed on Dec. 28, 2018, the entire disclosures of which are hereby incorporated by reference.

BACKGROUND

Field

The present specification generally relates to catalysts that efficiently convert various carbon-containing streams to $C_2$ to $C_4$ olefins. In particular, the present specification relates to preparation of hybrid catalysts and application of process methods to achieve a high conversion of synthesis gas feeds resulting in good conversion of carbon and high yield of desired products. The synthesis gas comprises hydrogen gas and a carbon-containing gas selected from the group consisting of carbon monoxide, carbon dioxide, and mixtures thereof. A hybrid catalyst generally comprises a combination of a metal oxide component and a microporous catalyst component that operate in tandem.

Technical Background

For a number of industrial applications, olefins are used, or are starting materials used, to produce plastics, fuels, and various downstream chemicals. Such olefins include $C_2$ to $C_4$ materials, such as ethylene, propylene, and butylenes (also commonly referred to as ethene, propene and butenes, respectively). A variety of processes for producing these lower olefins have been developed, including petroleum cracking and various synthetic processes.

Synthetic processes for converting feed carbon to desired products, such as olefins, are known. Some of these synthetic processes begin with use of a hybrid catalyst. Different types of catalysts have also been explored, as well as different kinds of feed streams and proportions of feed stream components. However, many of these synthetic processes have low carbon conversion and much of the feed carbon either (1) does not get converted and exits the process in the same form as the feed carbon; (2) is converted to $CO_2$; or (3) these synthetic processes have low stability over time and the catalyst rapidly loses its activity for carbon conversion to desirable products. For example, many synthetic processes tend to have increased methane production—and, thus, decreased $C_2$ to $C_4$ olefin production—over time.

Accordingly, a need exists for processes and catalytic systems that have a high conversion of feed carbon to desired products, such as, for example, $C_2$ to $C_4$ olefins in combination with a high on stream stability of the catalyst.

SUMMARY

According to one embodiment, a process for preparing $C_2$ to $C_4$ olefins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_4$ olefins in the reaction zone in the presence of the hybrid catalyst, the hybrid catalyst comprising: a metal oxide catalyst component comprising gallium oxide and phase pure zirconia; and a microporous catalyst component.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of hybrid catalysts and methods using the hybrid catalyst to prepare $C_2$ to $C_4$ olefins. In one embodiment, a process for preparing $C_2$ to $C_4$ olefins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_4$ olefins in the reaction zone in the presence of the hybrid catalyst, the hybrid catalyst comprising: a metal oxide catalyst component comprising gallium oxide and phase pure zirconia; and a microporous catalyst component.

The use of hybrid catalysts to convert feed streams comprising carbon to desired products, such as, for example, $C_2$ to $C_4$ olefins, is known. However, many known hybrid catalysts are inefficient, because they exhibit a low feed carbon conversion and/or deactivate quickly as they are used, such as, for example, by having an increase in methane production, which leads to a low olefin yield and low stability for a given set of operating conditions over a given amount of time. In contrast, hybrid catalysts disclosed and described herein exhibit a high and steady yield of $C_2$ to $C_4$ olefins, even as the catalyst time on stream increases. The composition of such hybrid catalysts used in embodiments is discussed below.

As a summary, hybrid catalysts closely couple independent reactions on each of the two independent catalysts. In the first step, a feed stream comprising hydrogen gas ($H_2$) and at least one of carbon monoxide (CO), carbon dioxide ($CO_2$), or a mixture of CO and $CO_2$, such as, for example, syngas, is converted into an intermediate(s) such as oxygenated hydrocarbons. In the subsequent step, these intermediates are converted into hydrocarbons (mostly short chain hydrocarbons, such as, for example $C_2$ to $C_4$ olefins). The continued formation and consumption of the intermediate oxygenates formed in the first step by the reactions of the second step ensures that there is no thermodynamic limit on conversions. With a careful selection of the components to the hybrid catalytic bed, high conversions of the syngas feed can be achieved.

Hybrid catalyst systems comprise a metal oxide catalyst component, which converts the feed stream to oxygenated hydrocarbons, and a microporous catalyst component (such as, for example, a silicoaluminophosphate or SAPO-type molecular sieve component), which converts the oxygenated hydrocarbons to hydrocarbons. Known hybrid catalyst systems based on chromium-zinc mixed metal oxide catalyst generally exhibit a trade-off between initial yield of $C_2$ to $C_4$ olefins and sustained yield of $C_2$ to $C_4$ olefins as the catalyst time on stream increases (also referred to as stability). There is accordingly a need for a metal oxide catalyst component that results in a high initial yield as well as a high stability when combined with a microporous catalyst component in a hybrid catalyst process. It should be understood that, as used herein, the "metal oxide catalyst component" includes metals in various oxidation states. In some embodiments, the metal oxide catalyst component may comprise more than one metal oxide and individual metal oxides within the metal oxide catalyst component may have different oxidation states. Thus, the metal oxide catalyst component is not limited to comprising metal oxides with homogenous oxidation states.

Embodiments of hybrid catalysts and systems for using hybrid catalysts disclosed herein comprise a metal oxide catalyst component comprising: (1) gallium (Ga), and (2) phase pure zirconia ($ZrO_2$). In some embodiments, the phase pure zirconia may be crystalline, and in some embodiments, the phase pure zirconia may be monoclinic crystalline phase pure zirconia. The metal oxide catalyst component is combined with a microporous catalyst component. The microporous catalyst component is, according to some embodiments, an 8-MR microporous catalyst component, such as, for example, SAPO-34 molecular sieve.

Metal oxide catalyst components for use in a hybrid catalyst according to embodiments will now be described. As referred to above, metals commonly used as constituents of the metal oxide catalyst component of some hybrid catalysts include combinations of zinc (Zn) and chromium (Cr). However, catalysts comprising zinc and chromium, which are known as high temperature methanol synthesis catalysts, do not have a combination of good olefin yield and good stability when kept on stream for an extended period of time. Although other metal combinations have been used, zinc and chromium have long been thought to be the most efficient metal oxide components for producing lower olefins, such as $C_2$ to $C_4$ olefins.

Gallium oxide (gallia, $Ga_2O_3$) is a very capable promoter for methanol-forming catalysts that are based on palladium, copper or nickel. In such functions, it is believed that upon reduction in the presence of hydrogen gallium oxide forms sub-oxides and surface hydrides. Eventually, the reduction process may lead to alloying of Ga metal with the active catalyst component (Pd, Cu or Ni) creating a better performing intermetallic phase such (e.g., Pd—Ga). In contrast, gallium oxides and supported gallium oxides show very poor performance in conversion of syngas. Further, bulk neat gallia used as a metal oxide component of a hybrid catalyst generally yields a high percentage of paraffins. However, it was unexpectedly found that when gallia was combined with a phase pure zirconia this combination promoted both the high olefin yield and high process stability of the hybrid catalyst.

As used herein, the zirconia used in embodiments disclosed and described herein in the metal oxide catalyst component of the hybrid catalyst is "phase pure zirconia", which is defined herein as zirconia to which no other materials have intentionally been added during formation. Thus, "phase pure zirconia" includes zirconia with small amounts of components other than zirconium (including oxides other than zirconia) that are unintentionally present in the zirconia as a natural part of the zirconia formation process, such as, for example, hafnium (Hf). Accordingly, as used herein "zirconia" and "phase pure zirconia" are used interchangeably unless specifically indicated otherwise.

Without being bound by any particular theory, it is believed that the high surface area of zirconia allows the gallium oxide catalyst acting as part of hybrid catalyst to convert carbon-containing components to $C_2$ to $C_4$ olefins. It is believed that the gallium oxide and the zirconia oxide help to activate one another, which results in improved yield for $C_2$ to $C_4$ olefins.

Surprisingly, along the high activity and high selectivity of the unique combination of $Ga/ZrO_2$ component used to prepare hybrid catalysts with a molecular sieve, it has been found that such hybrid catalysts comprising gallium oxide and zirconia as its metal oxide component have improved stability in extended process times. It was also found, in embodiments, that crystalline zirconia is a particularly effective carrier for gallium oxide. Moreover, in some embodiments, it was found that monoclinic zirconia is a particularly good carrier for gallium oxide that provides combined very high activity without compromising the selectivity for $C_2$ to $C_4$ olefins.

In embodiments disclosed herein, the composition of the metal oxide catalyst component is designated by a weight percentage of the gallium metal to the pure zirconia (accounting for $ZrO_2$ stoichiometry). In one or more embodiments, the composition of the metal oxide catalyst component is designated by weight of gallium per 100 grams (g) of zirconia. According to embodiments, the metal oxide catalyst component comprises from greater than 0.0 g gallium to 30.0 g gallium per 100 g of zirconia, such as 5.0 g gallium to 30.0 g gallium per 100 g of zirconia, 10.0 g gallium to 30.0 g gallium per 100 g of zirconia, 15.0 g gallium to 30.0 g gallium per 100 g of zirconia, 20.0 g gallium to 30.0 g gallium per 100 g of zirconia, or 25.0 g gallium to 30.0 g gallium per 100 g of zirconia. In some embodiments, the metal oxide catalyst component comprises from greater than 0.0 g gallium to 25.0 g gallium per 100 g of zirconia, such as from greater than 0.0 g gallium to 20.0 g gallium per 100 g of zirconia, from greater than 0.0 g gallium to 15.0 g gallium per 100 g of zirconia, from greater than 0.0 g gallium to 10.0 g gallium per 100 g of zirconia, or from greater than 0.0 g gallium to 5.0 g gallium per 100 g of zirconia. In some embodiments, the metal oxide catalyst component comprises from 5.0 g gallium to 25.0 g gallium per 100 g of zirconia, such as from 10.0 g gallium to 20.0 g gallium per 100 g of zirconia. In some embodiments, the metal oxide catalyst component comprises from 0.01 g gallium per 100 g of zirconia to 5.00 g gallium to 100 g zirconia, such as from 0.50 g gallium per 100 g of zirconia to 5.00 g gallium to 100 g zirconia, from 1.00 g gallium per 100 g of zirconia to 5.00 g gallium to 100 g zirconia, from 1.50 g gallium per 100 g of zirconia to 5.00 g gallium to 100 g zirconia, from 2.00 g gallium per 100 g of zirconia to 5.00 g gallium to 100 g zirconia, from 2.50 g gallium per 100 g of zirconia to 5.00 g gallium to 100 g zirconia, from 3.00 g gallium per 100 g of zirconia to 5.00 g gallium to 100 g zirconia, from 3.50 g gallium per 100 g of zirconia to 5.00 g gallium to 100 g zirconia, from 4.00 g gallium per 100 g of zirconia to 5.00 g gallium to 100 g zirconia, or from 4.50 g gallium per 100 g of zirconia to 5.00 g gallium to 100 g zirconia.

As disclosed herein above, and without being bound to any particular theory, it is understood that the high-surface area zirconia acts as a support or carrier for the gallium constituent of the metal oxide component, which yields a gallium and zirconia metal oxide catalyst component that will have selectivity for producing $C_2$ to $C_4$ olefins. Accordingly, it has been found that processes for making the gallium and zirconia metal oxide catalyst that require intimate contact of the gallium and zirconium components yield metal oxide catalyst components that have improved selectivity for $C_2$ to $C_4$ olefins.

In view of the above, one method for making the gallium and zirconium metal oxide component of the hybrid catalyst is by incipient wetness impregnation. In such a method, an aqueous mixture of a gallium precursor material, which, in embodiments, may be gallium nitrate ($Ga(NO_3)_3$) is added to zirconia particles in a dosed amount (such as dropwise) while vigorously shaking the zirconia particles. It should be understood that the total amount of gallium precursor that is mixed with the zirconia particles will be determined on the desired target amount of gallium in metal oxide catalyst component.

As discussed previously, according to some embodiments, the zirconia particles comprise zirconia particles having a crystalline structure. In embodiments, the zirconia particles comprise zirconia particles having a monoclinic structure. In one or more embodiments, the zirconia particles consist essentially of or consist of crystalline zirconia particles, and in some embodiments, the zirconia particles consist essentially of or consist of monoclinic zirconia particles. According to some embodiments, the zirconia particles have a BET surface area that is greater than or equal to 5 meters squared per gram ($m^2/g$), such as greater than 10 $m^2/g$, greater than 20 $m^2/g$, greater than 30 $m^2/g$, greater than 40 $m^2/g$, greater than 50 $m^2/g$, greater than 60 $m^2/g$, greater than 70 $m^2/g$, greater than 80 $m^2/g$, greater than 90 $m^2/g$, greater than 100 $m^2/g$, greater than 110 $m^2/g$, greater than 120 $m^2/g$, greater than 130 $m^2/g$, or greater than 140 $m^2/g$. According to some embodiments, the maximum BET surface area of the zirconia particles is 150 $m^2/g$. Accordingly, in some embodiments, the BET surface area of the zirconia particles is from 5 $m^2/g$ to 150 $m^2/g$, from 10 $m^2/g$ to 150 $m^2/g$, from 20 $m^2/g$ to 150 $m^2/g$, such as from 30 $m^2/g$ to 150 $m^2/g$, from 40 $m^2/g$ to 150 $m^2/g$, from 50 $m^2/g$ to 150 $m^2/g$, from 60 $m^2/g$ to 150 $m^2/g$, from 70 $m^2/g$ to 150 $m^2/g$, from 80 $m^2/g$ to 150 $m^2/g$, from 90 $m^2/g$ to 150 $m^2/g$, from 100 $m^2/g$ to 150 $m^2/g$, from 110 $m^2/g$ to 150 $m^2/g$, from 120 $m^2/g$ to 150 $m^2/g$, from 130 $m^2/g$ to 150 $m^2/g$, or from 140 $m^2/g$ to 150 $m^2/g$. In some embodiments, the BET surface area of the zirconia particles is from 5 $m^2/g$ to 140 $m^2/g$, such as from 5 $m^2/g$ to 130 $m^2/g$, from 5 $m^2/g$ to 120 $m^2/g$, from 5 $m^2/g$ to 110 $m^2/g$, from 5 $m^2/g$ to 100 $m^2/g$, from 5 $m^2/g$ to 90 $m^2/g$, from 5 $m^2/g$ to 80 $m^2/g$, from 5 $m^2/g$ to 70 $m^2/g$, from 5 $m^2/g$ to 60 $m^2/g$, from 5 $m^2/g$ to 50 $m^2/g$, from 5 $m^2/g$ to 40 $m^2/g$, from 5 $m^2/g$ to 30 $m^2/g$, from 5 $m^2/g$ to 20 $m^2/g$, or from 5 $m^2/g$ to 10 $m^2/g$. In some embodiments, the BET surface area of the zirconia particles is from 10 $m^2/g$ to 140 $m^2/g$, from 20 $m^2/g$ to 130 $m^2/g$, from 30 $m^2/g$ to 120 $m^2/g$, from 40 $m^2/g$ to 110 $m^2/g$, from 50 $m^2/g$ to 100 $m^2/g$, from 60 $m^2/g$ to 90 $m^2/g$, or from 70 $m^2/g$ to 80 $m^2/g$.

Once the gallium precursor and zirconia particles are adequately mixed, the metal oxide catalyst component may be dried at temperatures less than 200 degrees Celsius (° C.), such as less than 175° C., or less than 150° C. Subsequent to the drying, the metal oxide catalyst component is calcined at temperatures from 400° C. to 800° C., such as from 425° C. to 775° C., from 450° C. to 750° C., from 475° C. to 725° C., from 500° C. to 700° C., from 525° C. to 675° C., from 550° C. to 650° C., from 575° C. to 625° C., or about 600° C. After calcining, the composition of the mixed metal oxide catalyst component is determined and reported as a weight of elemental gallium referenced per 100 g of phase pure zirconia (simplified to the stoichiometry of $ZrO_2$) as previously disclosed above.

In embodiments, the metal oxide catalyst component may be made by mixing powders or slurries of a gallium precursor (such as gallium nitrate or gallium oxide) and zirconia. According to some embodiments, the zirconia particles comprise zirconia particles having a crystalline structure. In embodiments, the zirconia particles comprise zirconia particles having a monoclinic structure. In one or more embodiments, the zirconia particles consist essentially of or consist of crystalline zirconia particles, and in some embodiments, the zirconia particles consist essentially of or consist of monoclinic zirconia particles. The zirconia particles may, in embodiments, have the BET surface areas disclosed above. The powders or slurries may be vigorously mixed at high temperatures such from room temperature (approximately 23° C.) to 100° C. After the powders or slurries have been adequately mixed, the metal oxide catalyst component may be dried and calcined at temperatures from 400° C. to 800° C., such as from 425° C. to 775° C., from 450° C. to 750° C., from 475° C. to 725° C., from 500° C. to 700° C., from 525° C. to 675° C., from 550° C. to 650° C., from 575° C. to 625° C., or about 600° C. After calcining, the composition of the mixed metal oxide catalyst component is determined and reported as a weight of elemental gallium in reference to 100 g of phase pure zirconia (simplified to the stoichiometry of $ZrO_2$) as disclosed above.

It should be understood that according to embodiments, the metal oxide catalyst component may be made by other methods that eventually lead to intimate contact between the gallium and zirconia. Some non-limiting instances include vapor phase deposition of Ga-containing precursors (either organic or inorganic in nature), followed by their controlled decomposition. Similarly, processes for dispersing liquid gallium metal can be amended by those skilled in the art to develop Ga—$ZrO_2$.

Elements other than zirconia and gallium may, in some embodiments, be present in the metal oxide catalyst component containing phase pure zirconia and gallium. Such elements may be introduced to the phase pure zirconia before, during or after introducing gallium to the composition. Sometimes such elements are added to direct and stabilize the crystallization of zirconia phase (e.g., Y-stabilized tetragonal $ZrO_2$). In other instances, additional elements from the group of rare earth, alkaline, and/or transition metals are co-deposited with gallium precursor or introduced only when Ga—$ZrO_2$ mixed composition has been prepared in the first place. Similarly, the metal oxide catalyst component may also contain residual or be purposefully modified with non-metal dopants like, for example, sulfur (present as, for example, oxoanion $SO_4$), chlorine (Cl), phosphorus (P), or mixtures thereof may be present in the zirconia support or remain after using as an element of the precursor intended to introduce gallium or other metals into the phase-pure zirconia.

In one or more embodiments, after the metal oxide catalyst component has been formed—such as, for example, by the methods disclosed above—the metal oxide catalyst component is physically mixed with a microporous catalyst component. The microporous catalyst component is, in embodiments, selected from molecular sieves having 8-MR pore openings and having a framework type selected from the group consisting of the following framework types CHA, AEI, AFX, ERI, LTA, UFI, RTH, EDI, GIS, MER, RHO, and combinations thereof, the framework types corresponding to the naming convention of the International Zeolite Association. It should be understood that in embodiments, both aluminosilicate and silicoaluminophosphate frameworks may be used. Some embodiments may include tetrahedral aluminosilicates, ALPOs (such as, for example, tetrahedral aluminophosphates), SAPOs (such as, for example, tetrahedral silicoaluminophosphates), and silica-only based tectosilicates. In certain embodiments, the microporous catalyst component may be silicoaluminophosphate having a Chabazite (CHA) framework type. Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have different membered ring pore opening depending on the desired product. For instance, microporous catalyst component having 8-MR to 12-MR pore openings could be used depending on the desired product. However, to produce $C_2$ to $C_4$ olefins, a microporous catalyst component having 8-MR pore openings is used in embodiments.

The metal oxide catalyst component and the microporous catalyst component of the hybrid catalyst may be mixed together by any suitable means, such as, for example, by physical mixing—such as shaking, stirring, or other agitation. The metal oxide catalyst component may, in embodiments, comprise from 1.0 wt % to 99.0 wt % of the hybrid catalyst, such as from 5.0 wt % to 99.0 wt %, from 10.0 wt % to 99.0 wt %, from 15.0 wt % to 99.0 wt %, from 20.0 wt % to 99.0 wt %, from 25.0 wt % to 99.0 wt %, from 30.0 wt % to 99.0 wt %, from 35.0 wt % to 99.0 wt %, from 40.0 wt % to 99.0 wt %, from 45.0 wt % to 99.0 wt %, from 50.0 wt % to 99.0 wt %, from 55.0 wt % to 99.0 wt %, from 60.0 wt % to 99.0 wt %, from 65.0 wt % to 99.0 wt %, from 70.0 wt % to 99.0 wt %, from 75.0 wt % to 99.0 wt %, from 80.0 wt % to 99.0 wt %, from 85.0 wt % to 99.0 wt %, from 90.0 wt % to 99.0 wt %, or from 95.0 wt % to 99.0 wt %. In some embodiments, the metal oxide catalyst component comprises from 1.0 wt % to 95.0 wt % of the hybrid catalyst, such as from 1.0 wt % to 90.0 wt %, from 1.0 wt % to 85.0 wt %, from 1.0 wt % to 80.0 wt %, from 1.0 wt % to 75.0 wt %, from 1.0 wt % to 70.0 wt %, from 1.0 wt % to 65.0 wt %, from 1.0 wt % to 60.0 wt %, from 1.0 wt % to 55.0 wt %, from 1.0 wt % to 50.0 wt %, from 1.0 wt % to 45.0 wt %, from 1.0 wt % to 40.0 wt %, from 1.0 wt % to 35.0 wt %, from 1.0 wt % to 30.0 wt %, from 1.0 wt % to 25.0 wt %, from 1.0 wt % to 20.0 wt %, from 1.0 wt % to 15.0 wt %, from 1.0 wt % to 10.0 wt %, or from 1.0 wt % to 5.0 wt %. In some embodiments, the metal oxide catalyst component comprises from 5.0 wt % to 95.0 wt % of the hybrid catalyst, such as from 10.0 wt % to 90.0 wt %, from 15.0 wt % to 85.0 wt %, from 20.0 wt % to 80.0 wt %, from 25.0 wt % to 75.0 wt %, from 30.0 wt % to 70.0 wt %, from 35.0 wt % to 65.0 wt %, from 40.0 wt % to 60.0 wt %, or from 45.0 wt % to 55.0 wt %.

After the metal oxide catalyst component has been formed and combined with a microporous catalyst component to form a hybrid catalyst, the hybrid catalyst may be used in methods for converting carbon in a carbon-containing feed stream to $C_2$ to $C_4$ olefins. Such processes will be described in more detail below.

According to embodiments, a feed stream is fed into a reaction zone, the feed stream comprising hydrogen ($H_2$) gas and a carbon-containing gas selected from carbon monoxide (CO), carbon dioxide (CO2), and combinations thereof. In some embodiments, the $H_2$ gas is present in the feed stream in an amount of from 10 volume percent (vol %) to 90 vol %, based on combined volumes of the $H_2$ gas and the gas selected from CO, $CO_2$, and combinations thereof. The feed stream is contacted with a hybrid catalyst as disclosed and described herein in the reaction zone. The hybrid catalyst comprises a metal oxide catalyst component comprising gallium oxide and zirconia; and a microporous catalyst component.

It should be understood that the activity of the hybrid catalyst will be higher for feed streams containing CO as the carbon-containing gas, and that the activity of the hybrid catalyst decreases as a larger portion of the carbon-containing gas in the feed stream is $CO_2$. However, that is not to say that the hybrid catalyst disclosed and described herein cannot be used in methods where the feed stream comprises $CO_2$ as all, or a large portion, of the carbon-containing gas.

The feed stream is contacted with the hybrid catalyst in the reaction zone under reaction conditions sufficient to form a product stream comprising $C_2$ to $C_4$ olefins. The reaction conditions comprise a temperature within the reaction zone ranging, according to one or more embodiments, from 300° C. to 500° C., such as from 300° C. to 475° C., from 300° C. to 450° C., from 300° C. to 425° C., from 300° C. to 400° C., from 300° C. to 375° C., from 300° C. to 350° C., or from 300° C. to 325° C. In other embodiments, the temperature within the reaction zone is from 325° C. to 500° C., from 350° C. to 500° C., from 375° C. to 500° C., from 400° C. to 500° C., from 425° C. to 500° C., from 450° C. to 500° C., or from 475° C. to 500° C. In yet other embodiments, the temperature within the reaction zone is from 300° C. to 500° C., such as from 325° C. to 475° C., from 350° C. to 450° C., or from 360° C. to 440° C.

The reaction conditions also, in embodiments, include a pressure inside the reaction zone of at least 1 bar (100 kilopascals (kPa), such as at least 5 bar (500 kPa), at least 10 bar (1,000 kPa), at least 15 bar (1,500 kPa), at least 20 bar (2,000 kPa), at least 25 bar (2,500 kPa), at least 30 bar (3,000 kPa), at least 35 bar (3,500 kPa), at least 40 bar (4,000 kPa), at least 45 bar (4,500 kPa), at least 50 bar (5,000 kPa), at least 55 bar (5,500 kPa), at least 60 bar (6,000 kPa), at least 65 bar (6,500 kPa), at least 70 bar (7,000 kPa), at least 75 bar (7,500 kPa), at least 80 bar (8,000 kPa), at least 85 bar (8,500 kPa), at least 90 bar (9,000 kPa), at least 95 bar (9,500 kPa), or at least 100 bar (10,000 kPa). In other embodiments, the reaction conditions include a pressure inside the reaction zone is from 5 bar (500 kPa) to 100 bar (10,000 kPa), such as from 10 bar (1,000 kPa) to 95 bar (9,500 kPa), from 15 bar (1,500 kPa) to 90 bar (9,000 kPa), from 20 bar (2,000 kPa) to 85 bar (8,500 kPa), from 25 bar (2,500 kPa) to 80 bar (8,000 kPa), from 30 bar (3,000 kPa) to 75 bar (7,500 kPa), from 35 bar (3,500 kPa) to 70 bar (7,000 kPa), from 40 bar (4,000 kPa) to 65 bar (6,500 kPa), from 45 bar (4,500 kPa) to 60 bar (6,000 kPa), or from 50 bar (5,000 kPa) to 55 bar (5,500 kPa). In some embodiments, the pressure inside the reaction zone is from 20 bar (2,000 kPa) to 60 bar (6,000 kPa).

According to embodiments, the gas hour space velocity (GHSV) within the reaction zone is from 1,200 per hour (/h) to 12,000/h, such as from 1,500/h to 10,000/h, from 2,000/h to 9,500/h, from 2,500/h to 9,000/h, from 3,000/h to 8,500/h, from 3,500/h to 8,000/h, from 4,000/h to 7,500/h, from 4,500/h to 7,000/h, from 5,000/h to 6,500/h, or from 5,500/h to 6,000/h. In some embodiments the GHSV within the reaction zone is from 1,800/h to 3,600/h, such as from 2,000/h to 3,600/h, from 2,200/h to 3,600/h, from 2,400/h to 3,600/h, from 2,600/h to 3,600/h, from 2,800/h to 3,600/h, from 3,000/h to 3,600/h, from 3,200/h to 3,600/h, or from 3,400/h to 3,600/h. In some embodiments, the GHSV within the reaction zone is from 1,800/h to 3,400/h, such as from 1,800/h to 3,200/h, from 1,800/h to 3,000/h, from 1,800/h to 2,800/h, from 1,800/h to 2,600/h, from 1,800/h to 2,400/h, from 1,800/h to 2,200/h, or from 1,800/h to 2,000/h. In some embodiments, the GHSV within the reaction is from 2,000/h to 3,400/h, such as from 2,200/h to 3,200/h, from 2,400/h to 3,000/h, or from 2,600/h to 2,800/h.

By using hybrid catalysts disclosed and described herein along with the process conditions disclosed and described herein, improved $C_2$ to $C_4$ olefin yields and carbon conversion may be achieved. For example, in embodiments where hydrogen to carbon monoxide $H_2$/CO ratios range from 2 to 5, such as greater than 2.2 and less than 3.8, or greater than 2.8 and less than 3.4, where temperatures range from 360° C. to 460° C., such as from 380° C. to 440° C., or from 400° C. to 420° C., and pressure ranges from 5 to 100 bars, such as from 20 to 80 bars, or from 30 to 60 bars. Using such conditions, the $C_2$ to $C_4$ olefin yield is greater than or equal to 4.0 mol %, such as greater than or equal to 5.0 mol %, greater than or equal to 7.0 mol %, greater than or equal to 10.0 mol %, greater than or equal to 12.0 mol %, greater than or equal to 15.0 mol %, greater than or equal to 17.0 mol %, greater than or equal to 20.0 mol %, greater than or equal to 22.0 mol %, greater than or equal to 25.0 mol %, greater than or equal to 27.0 mol %, greater than or equal to 30.0 mol %, greater than or equal to 32.0 mol %, or greater than or equal to 35.0 mol %. In some embodiments, the maximum $C_2$ to $C_4$ olefin yield is 50.0 mol %. Thus, in some embodiments, the $C_2$ to $C_4$ olefin yield is from greater than or equal to 4.0 mol % to 50.0 mol %, such as from 5.0 mol % to 50.0 mol %, from 7.0 mol % to 50.0 mol %, from 10.0 mol % to 50.0 mol %, from 12.0 mol % to 50.0 mol %, from 15.0 mol % to 50.0 mol %, from 17.0 mol % to 50.0 mol %, from 20.0 mol % to 50.0 mol %, from 22.0 mol % to 50.0 mol %, from 25.0 mol % to 50.0 mol %, from 27.0 mol % to 50.0 mol %, from 30.0 mol % to 50.0 mol %, from 32.0 mol % to 50.0 mol %, from 35.0 mol % to 50.0 mol %, from 37.0 mol % to 50.0 mol %, from 40.0 mol % to 50.0 mol %, from 42.0 mol % to 50.0 mol %, from 45.0 mol % to 50.0 mol %, or from 47.0 mol % to 50.0 mol %.

In embodiments, using hybrid catalysts disclosed and described herein along with the process conditions disclosed and described herein, the carbon conversion may be improved. Within the process ranges disclosed, the conversion of the feed containing carbon oxides and hydrogen can be carried out in a series of rectors with an intermediate knock-out of water by-product by the means of e.g., phase separation, membrane separation, or some type of water-selective absorptive process. Further directing the partially converted and water-free effluent to the subsequent reactor in series and repeating this manner of technological operations will have an overall effect of enhancing the olefin yield. For example, in embodiments where two to four such operations are carried out the overall olefin yield may be greater than or equal to 50.0 mol %, such as greater than or equal to 52.0 mol %, greater than or equal to 55.0 mol %, greater than or equal to 57.0 mol %, greater than or equal to 60.0 mol %, greater than or equal to 62.0 mol %, greater than or equal to 65.0 mol %, greater than or equal to 67.0 mol %, greater than or equal to 70.0 mol %, greater than or equal to 72.0 mol %, greater than or equal to 75.0 mol %, greater than or equal to 77.0 mol %, greater than or equal to 80.0 mol %, or greater than or equal to 85.0 mol %. In some embodiments, the maximum carbon conversion is 95.0 mol %. Accordingly, in embodiments, the carbon conversion may be from greater than or equal to 50.0 mol % to 95.0 mol %, such as from 52.0 mol % to 95.0 mol %, from 55.0 mol % to 95.0 mol %, from 57.0 mol % to 95.0 mol %, from 60.0 mol % to 95.0 mol %, from 62.0 mol % to 95.0 mol %, from 65.0 mol % to 95.0 mol %, from 67.0 mol % to 95.0 mol %, from 60.0 mol % to 95.0 mol %, from 72.0 mol % to 95.0 mol %, from 75.0 mol % to 95.0 mol %, from 77.0 mol % to 95.0 mol %, from 80.0 mol % to 95.0 mol %, from 82.0 mol % to 95.0 mol %, from 85.0 mol % to 95.0 mol %, from 87.0 mol % to 95.0 mol %, from 90.0 mol % to 95.0 mol %, or from 92.0 mol % to 95.0 mol %.

EXAMPLES

Embodiments will be further clarified by the following examples and comparative examples. In all examples and comparative examples hybrid catalysts were prepared by mixing the given amount of mixed oxide catalyst component (60-80 mesh) with microporous catalyst component SAPO-34 (60-80 mesh). The amounts can be found in the tables below. However, it should be understood that in some comparative examples, SAPO-34 is not included. This is indicated by a value of zero ("0") in the tables below.

Comparative Example 1

Composite catalysts with SAPO-34 microporous catalyst components and either bulk $In_2O_3$, bulk $Ga_2O_3$, or bulk $ZrO_2$; physical mixture of bulk $Ga_2O_3$ and $ZrO_2$ without microporous catalyst component.

Table 1a shows the results a process for converting syngas into olefins with the following process conditions: $H_2$/CO of approximately 2.0; pressure of 20 bar (2,000 kPa); temperature of 390° C., and GHSV equals 1200/h. The metal oxide catalyst used in the comparative example is a bulk metal oxide as shown in Table 1a. The indium oxide used in this comparative example was commercially available from Aldrich, product no. 63 2317, and the gallium oxide used was commercially available from Aldrich, product no. 20,333-5. Prior to this test each of the starting components were compacted, crushed and sized to provide 60-80 mesh fractions for the preparation of physical mixtures. Next, by combining 150 μL of SAPO-34 (approximately, sized particles) and adding 150 μL of either indium oxide or gallium oxide (each measured approximately, sized particles) hybrid catalysts were prepared upon gentle shaking of particles together in a vial. The table below references the catalytic performance of the dual-particle bed of SAPO-34 admixed with either of the neat oxides including each component weight.

TABLE 1a

| Oxide component present in admixture with SAPO-34 | SAPO-34 weight (mg) | Oxide weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] | Olefin Fraction in [$C_2$-$C_3$ Product] |
|---|---|---|---|---|---|---|---|
| | | | ToS = 12-24 hrs | | | | |
| $In_2O_3$ | 87 | 201 | 9.8 | 27.3 | 37.2 | 9.3 | 0.80 |
| $Ga_2O_3$ | 79 | 109 | 0.8 | 19.4 | 4.1 | 34.2 | 0.11 |

TABLE 1a-continued

| | | | ToS = 48-72 hrs | | | | |
|---|---|---|---|---|---|---|---|
| In$_2$O$_3$ | 87 | 201 | 0.2 | 1.2 | 16.1 | 8.5 | 0.65 |
| Ga$_2$O$_3$ | 79 | 109 | 0.8 | 18.9 | 4.2 | 34.1 | 0.11 |

| Oxide component present in admixture with SAPO-34 | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|
| | ToS = 12-24 hrs | | | |
| In$_2$O$_3$ | 2.9 | 1.1 | 0.8 | 51.1 |
| Ga$_2$O$_3$ | 2.6 | 0.0 | 9.2 | 49.6 |
| | ToS = 48-72 hrs | | | |
| In$_2$O$_3$ | 34.9 | 0.0 | 0.0 | 43.6 |
| Ga$_2$O$_3$ | 3.1 | 0.0 | 9.4 | 48.7 |

Table 1b shows results for a process for converting syngas into olefins, at the following process conditions: H$_2$/CO of approximately 3.0; pressure of 40 bar (4,000 kPa); temperature of 420° C.; and GHSV equals 2400/h and compares intrinsic performance of either zirconia or gallia admixed with SAPO-34. The zirconium oxide used in this comparative example was commercially available monoclinic ZrO$_2$, (vendor NORPRO, product code SZ39114) and contains some Hf impurity (approximately 2.45 wt %). Before being used, the zirconium oxide was dispersed in water, dried, and calcined at 550° C. The gallium oxide used in this comparative example was commercially available gallium oxide (available as AlfaAesar, product no. 10508). Before being used, the gallium oxide is dispersed in water, dried, and calcined at 550° C. Prior to this test both oxides and the sieve were compacted, crushed and sieved to provide 60-80 mesh fractions of the starting components. Next, by measuring volumetrically approximately 200 μL of SAPO-34 (sized particles) and adding either 200 μL of zirconium oxide (sized particles) or 200 μL of gallium oxide (sized particles) hybrid catalysts were prepared upon gentle shaking. The table below references the catalytic performance of the dual-particle bed of SAPO-34 admixed with either of the neat oxides.

TABLE 1b

| Oxide component present in admixture with SAPO-34 | SAPO-34 Weight (mg) | Oxide Weight (mg) | Yield C$_2$-C$_3$ Olefins [C mol %] | CO Conv. [C mol. %] | Selectivity C$_2$-C$_3$ Olefin [C mol %] | Selectivity C$_2$-C$_3$ Paraffin [C mol %] |
|---|---|---|---|---|---|---|
| | | | ToS = 24-48 hrs | | | |
| ZrO$_2$ | 104 | 252 | 9.2 | 23.7 | 38.8 | 13.7 |
| Ga$_2$O$_3$ | 100 | 179 | 3.9 | 40.6 | 9.5 | 39.3 |
| | | | ToS = 72-96 hrs | | | |
| ZrO$_2$ | 104 | 252 | 10.0 | 26.1 | 38.3 | 14.7 |
| Ga$_2$O$_3$ | 100 | 179 | 3.4 | 38.0 | 8.8 | 39.5 |

| Oxide component present in admixture with SAPO-34 | Olefin Fraction in [C$_2$-C$_3$ Product] | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|---|
| | | ToS = 24-48 hrs | | | |
| ZrO$_2$ | 0.7 | 1.4 | 4.1 | 1.0 | 40.9 |
| Ga$_2$O$_3$ | 0.2 | 2.5 | 4.4 | 6.2 | 38.1 |
| | | ToS = 72-96 hrs | | | |
| ZrO$_2$ | 0.7 | 1.5 | 4.1 | 1.0 | 40.4 |
| Ga$_2$O$_3$ | 0.2 | 3.0 | 3.7 | 6.8 | 38.3 |

Table 1c shows results for a process for converting syngas into at the following process conditions: H$_2$/CO of approximately 3.0; pressure of 40 bar (4,000 kPa); temperature of 420° C.; and GHSV equals 2400/h. To prepare a dual-particle catalyst bed Zirconium oxide (20 mg) and gallium oxide (80 mg) were physically mixed together to form a mixture of particles (100 mg). To prepare this combination the ZrO$_2$ and Ga$_2$O$_3$ materials referenced in the example 1b, were used. To further differentiate this combination, the catalyst bed did not contain any SAPO-34 component.

TABLE 1c

| Oxide components present | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~18.4 g Ga/100 g $ZrO_2$ | 0.0 | 100.0 | 0.6 | 7.4 | 8.5 | 7.5 |
| ToS = 72-96 hrs | | | | | | |
| ~18.4 g Ga/100 g $ZrO_2$ | 0.0 | 100.0 | 0.6 | 7.4 | 7.7 | 6.7 |

| Oxide components present | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs | | | | | |
| ~18.4 g Ga/100 g $ZrO_2$ | 0.53 | 4.3 | 2.5 | 2.2 | 39.2 |
| ToS = 72-96 hrs | | | | | |
| ~18.4 g Ga/100 g ZrOi | 0.53 | 4.2 | 2.6 | 3.6 | 38.5 |

Comparative Example 1a demonstrates intrinsic properties of neat bulk oxides of elements from Group 13 of the periodic table of elements upon formulation of dual-particle bed with SAPO-34. Comparative example 1b benchmarks intrinsic properties of neat zirconia against neat gallia in combination with SAPO-34 in dual-particle bed application. This comparative example show that different neat oxides in combination with SAPO-34 results in very different catalytic behavior in the conversion of syngas to hydrocarbons. Notably, (1) neat $In_2O_3$ has a some initial high activity and selectivity towards olefins, but short life process time and the hybrid system deactivated rather quickly; (2) neat monoclinic $ZrO_2$ showed a high selectivity towards olefins and long life on stream but poor activity; (3) neat $Ga_2O_3$ showed moderate activity and very poor selectivity towards olefins and high selectivity to paraffins and at the same time could convert syngas over long process times than indium oxide. Furthermore, the comparative example 1c shows that a physical mixture of gallium and zirconium oxides without microporous catalyst component (SAPO-34) has also poor activity and low selectivity towards olefins.

Comparative Example 2

Table 2a shows the results a process for converting syngas into olefins with the following process conditions: $H_2$/CO of approximately 2; temperature of 390° C.; pressure of 20 bar (2,000 kPa); and GHSV equals 1200/h. The hybrid catalysts were prepared from the sized (60-80 mesh) particles of SAPO-34 (150 μL volumetric measure of sized particles or approximately 75 mg each time) and sized particles of various mixed metal oxide catalysts. The mixed oxides were featuring gallium and lacking zirconium. The oxides were prepared by incipient wetness impregnation of aqueous solutions of gallium nitrate precursor onto oxide of either silicon, titanium, or niobium followed by drying and calcination (500 dig). The amounts of the sized 60-80 mesh mixed oxide particles used to prepare hybrid catalyst beds with SAPO-34 were approximately 150 μL volumetric measure each time. Because of varied apparent densities of different carrier oxides, the weight of the oxides also varied. Hybrid catalysts were prepared upon gentle shaking of sized particles together in a vial.

TABLE 2a

| Oxide composition in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~3.8 g Ga/100 g $SiO_2$ | 70 | 49.7 | 0.3 | 2.6 | 12.0 | 16.5 |
| ~8.1 g Ga/100 g $SiO_2$ | 72 | 53.0 | 0.2 | 1.7 | 14.6 | 14.1 |
| ~11.6 g Ga/100 g $SiO_2$ | 70 | 54.0 | 0.3 | 3.5 | 10.0 | 16.6 |
| ~9.7 g Ga/100 g $TiO_2$ | 82 | 101.7 | 0.5 | 29.0 | 1.8 | 36.0 |
| ~3.5 g Ga/100 g $TiO_2$ | 81 | 103.1 | 1.0 | 26.8 | 3.9 | 31.5 |
| ~3.8 g Ga/100 g $Nb_2O_5$ | 88 | 144.1 | 0.1 | 3.9 | 2.3 | 14.4 |
| ToS = 72-96 hrs | | | | | | |
| ~3.8 g Ga/100 g $SiO_2$ | 70 | 49.7 | 0.3 | 2.7 | 10.5 | 16.5 |
| ~8.1 g Ga/100 g $SiO_2$ | 72 | 53.0 | 0.2 | 1.8 | 12.5 | 12.0 |
| ~11.6 g Ga/100 g $SiO_2$ | 70 | 54.0 | 0.3 | 3.3 | 8.7 | 16.4 |
| ~9.7 g Ga/100 g $TiO_2$ | 82 | 101.7 | 0.5 | 27.2 | 1.9 | 35.6 |
| ~3.5 g Ga/100 g $TiO_2$ | 81 | 103.0 | 1.0 | 25.5 | 4.1 | 31.3 |
| ~3.8 g Ga/100 g $Nb_2O_5$ | 88 | 144.1 | 0.1 | 3.9 | 2.3 | 13.8 |
| ToS = 100-120 hrs, $H_2$/CO ratio changed to 3, Pressure changed to 30 bar | | | | | | |
| ~9.7 g Ga/100 g $TiO_2$ | 82 | 101.7 | 0.5 | 33.2 | 1.5 | 37.3 |
| ~3.5 g Ga/100 g $TiO_2$ | 81 | 103.1 | 0.9 | 36.9 | 2.5 | 35.3 |

| Oxide composition in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs | | | | | |
| ~3.8 g Ga/100 g $SiO_2$ | 0.42 | 31.6 | 0.0 | 3.1 | 33.6 |
| ~8.1 g Ga/100 g $SiO_2$ | 0.51 | 21.2 | 0.0 | 0.0 | 45.2 |
| ~11.6 g Ga/100 g $SiO_2$ | 0.38 | 34.1 | 0.0 | 2.6 | 34.8 |
| ~9.7 g Ga/100 g $TiO_2$ | 0.05 | 7.4 | 0.3 | 7.3 | 47.2 |
| ~3.5 g Ga/100 g $TiO_2$ | 0.11 | 9.3 | 0.3 | 7.0 | 47.6 |
| ~3.8 g Ga/100 g $Nb_2O_5$ | 0.14 | 34.4 | 0.0 | 0.0 | 48.4 |
| ToS = 72-96 hrs | | | | | |
| ~3.8 g Ga/100 g $SiO_2$ | 0.39 | 32.6 | 0.0 | 2.9 | 32.0 |
| ~8.1 g Ga/100 g $SiO_2$ | 0.51 | 18.8 | 0.0 | 0.0 | 50.3 |
| ~11.6 g Ga/100 g $SiO_2$ | 0.35 | 34.8 | 0.0 | 2.7 | 33.7 |
| ~9.7 g Ga/100 g $TiO_2$ | 0.05 | 8.3 | 0.3 | 6.9 | 47.0 |
| ~3.5 g Ga/100 g $TiO_2$ | 0.12 | 9.9 | 0.4 | 6.7 | 47.0 |
| ~3.8 g Ga/100 g $Nb_2O_5$ | 0.14 | 33.8 | 0.0 | 0.0 | 49.3 |
| ToS = 100-120 hrs, $H_2$/CO ratio changed to 3, Pressure changed to 30 bar | | | | | |
| ~9.7 g Ga/100 g $TiO_2$ | 0.04 | 9.3 | 0.4 | 7.2 | 44.2 |
| ~3.5 g Ga/100 g $TiO_2$ | 0.07 | 8.4 | 0.1 | 6.9 | 45.7 |

Table 2b shows the results a process for converting syngas into olefins with the following process conditions: $H_2/CO$ of approximately 3; temperature of 420° C.; pressure of 40 bar (4,000 kPa); and GHSV equals 2400/h. The amounts of the sized 60-80 mesh mixed oxide particles used to prepare hybrid catalyst beds with SAPO-34 were approximately 200 μL volumetric measure each time. Hybrid catalysts were prepared upon gentle shaking of sized particles together in a vial.

TABLE 2b

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] | Olefin Fraction in [$C_2$-$C_3$ Product] |
|---|---|---|---|---|---|---|---|
| ToS = 24-48 hrs | | | | | | | |
| ~5.2 g Ga and ~5.7 g Zn/100 g $TiO_2$ | 126 | 150 | 3.5 | 58.9 | 5.9 | 42.4 | 0.12 |
| 9.4 g Ga/100 g $TiO_2$ | 127 | 146 | 1.4 | 46.8 | 3.1 | 29.4 | 0.10 |
| ToS = 72-86 hrs | | | | | | | |
| ~5.2 g Ga and ~5.7 g Zn/100 g $TiO_2$ | 126 | 150 | 3.0 | 58.1 | 5.2 | 41.2 | 0.11 |
| 9.4 g Ga/100 g $TiO_2$ | 127 | 146 | 1.4 | 43.8 | 3.1 | 27.5 | 0.10 |

| Oxide component present in admixture with SAPO-34 | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|
| ToS = 24-48 hrs | | | | |
| ~5.2 g Ga and ~5.7 g Zn/100 g $TiO_2$ | 6.0 | 1.6 | 8.3 | 35.8 |
| 9.4 g Ga/100 g $TiO_2$ | 18.9 | 1.0 | 5.9 | 41.7 |
| ToS = 72-96 hrs | | | | |
| ~5.2 g Ga and ~5.7 g Zn/100 g $TiO_2$ | 7.5 | 1.4 | 9.1 | 35.6 |
| ~9.4 g Ga/100 g $TiO_2$ | 21.2 | 0.9 | 5.5 | 41.8 |

For composite catalysts with SAPO-34 as the microporous catalyst component and a Ga-MOx metal oxide catalyst component. Each of the Ga-MOx metal oxide catalyst components was prepared by processing crystalline powders of either $Y_2O_3$, $La_2O_3$, $CeO_2$, $Cr_2O_3$, $MgAl_2O_4$, or MgO and $Ga_2O_3$ in slurring fine particles in deionized water, drying, and calcining at 550° C.

Table 2c shows the results a process for converting syngas into olefins with the following process conditions: $H_2/CO$ approximately 3; temperature of 420° C.; pressure of 40 bar (4,000 kPa); and GHSV equals 2400/h. The amounts of the sized 60-80 mesh mixed oxide particles used to prepare hybrid catalyst beds with SAPO-34 were approximately 200 μL volumetric measure each time. Hybrid catalysts were prepared upon gentle shaking of sized particles together in a vial.

TABLE 2c

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~12.9 wt % Ga, ~62.3 wt % Y, balance - oxygen | 101 | 147 | 1.3 | 19.4 | 6.5 | 40.3 |
| ~15.4 wt % Ga, ~66.5 wt % La, balance - oxygen | 116 | 190 | 0.9 | 16.7 | 5.3 | 38.8 |
| ~13.0 wt % Ga, ~66.1 wt % Ce, balance - oxygen | 111 | 211 | 3.0 | 26.0 | 11.6 | 37.5 |
| ~11.4 wt % Ga, ~57.4 wt % Cr, balance - oxygen | 99 | 152 | 1.8 | 17.8 | 10.1 | 43.9 |
| ~10.6 wt % Ga, ~31.3 wt % Al, ~15.7 wt % Mg, balance - oxygen | 98 | 183 | 0.8 | 5.8 | 13.1 | 24.7 |
| ~17.6 wt % Ga, ~45.2 wt % Mg, balance - oxygen | 95 | 218 | 0.9 | 9.3 | 9.5 | 31.9 |
| ToS = 72-96 hrs | | | | | | |
| ~12.9 wt % Ga, ~62.3 wt % Y, balance - oxygen | 101 | 147 | 1.1 | 19.1 | 6.0 | 38.1 |
| ~15.4 wt % Ga, ~66.5 wt % La, balance - oxygen | 116 | 190 | 0.9 | 16.3 | 5.7 | 36.2 |
| ~13.0 wt % Ga, ~66.1 wt % Ce, balance - oxygen | 111 | 211 | 2.4 | 24.8 | 9.7 | 39.1 |
| ~11.4 wt % Ga, ~57.4 wt % Cr, balance - oxygen | 99 | 152 | 1.4 | 16.8 | 8.6 | 44.9 |
| ~10.6 wt % Ga, ~31.3 wt % Al, ~15.7 wt % Mg, balance - oxygen | 98 | 183 | 0.8 | 5.9 | 12.8 | 21.3 |
| ~17.6 wt % Ga, ~45.2 wt % Mg, balance - oxygen | 95 | 218 | 0.9 | 8.6 | 10.4 | 28.2 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs | | | | | |
| ~12.9 wt % Ga, ~62.3 wt % Y, balance - oxygen | 0.14 | 4.5 | 2.6 | 6.8 | 39.4 |
| ~15.4 wt % Ga, ~66.5 wt % La, balance - oxygen | 0.12 | 5.3 | 1.0 | 9.1 | 40.4 |
| ~13.0 wt % Ga, ~66.1 wt % Ce, balance - oxygen | 0.24 | 3.4 | 4.9 | 4.0 | 38.6 |
| ~11.4 wt % Ga, ~57.4 wt % Cr, balance - oxygen | 0.19 | 2.4 | 4.0 | 5.2 | 34.4 |
| ~10.6 wt % Ga, ~31.3 wt % Al, ~15.7 wt % Mg, balance - oxygen | 0.35 | 15.1 | 0.0 | 6.7 | 40.5 |
| ~17.6 wt % Ga, ~45.2 wt % Mg, balance - oxygen | 0.23 | 9.0 | 1.8 | 8.8 | 39.0 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|

TABLE 2c-continued

| | | ToS = 72-96 hrs | | | |
|---|---|---|---|---|---|
| ~12.9 wt % Ga, ~62.3 wt % Y, balance - oxygen | 0.14 | 5.8 | 1.9 | 8.2 | 40.0 |
| ~15.4 wt % Ga, ~66.5 wt % La, balance - oxygen | 0.14 | 7.1 | 0.8 | 10.1 | 40.2 |
| ~13.0 wt % Ga, ~66.1 wt % Ce, balance - oxygen | 0.20 | 4.2 | 3.8 | 4.8 | 38.5 |
| ~11.4 wt % Ga, ~57.4 wt % Cr, balance - oxygen | 0.16 | 3.0 | 3.1 | 6.2 | 34.2 |
| ~10.6 wt % Ga, ~31.3 wt % Al, ~15.7 wt % Mg, balance - oxygen | 0.38 | 20.1 | 0.0 | 5.9 | 39.8 |
| ~17.6 wt % Ga, ~45.2 wt % Mg, balance - oxygen | 0.27 | 12.6 | 1.4 | 9.1 | 38.3 |

Example 1

This example shows the effects of hybrid catalysts formed from an SAPO-34 microporous catalyst component, and a metal oxide catalyst component comprising $ZrO_2$-supported gallium catalysts (monoclinic-$ZrO_2$, BET surface area of approximately 50 m²/g). The amounts of the sized 60-80 mesh mixed oxide particles used to prepare hybrid catalyst beds are reported in the Table 3a and 3b. Hybrid catalysts were prepared upon gentle shaking of particles together in a vial.

Table 3a shows the results a process for converting syngas into olefins with the following process conditions: $H_2/CO$ approximately 2; temperature of 390° C.; pressure of 20 bar (2,000 kPa); and GHSV equals 1200/h.

TABLE 3a

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| | | ToS = 24-48 hrs | | | | |
| ~9.3 g Ga/100 g $ZrO_2$ | 80 | 170 | 15.5 | 39.8 | 38.8 | 9.3 |
| ~3.3 g Ga/100 g $ZrO_2$ | 80 | 159 | 14.3 | 36.4 | 39.2 | 9.0 |
| | | ToS = 72-96 hrs | | | | |
| ~9.3 g Ga/100 g $ZrO_2$ | 80 | 170 | 14.9 | 38.5 | 38.6 | 9.0 |
| ~3.3 g Ga/100 g $ZrO_2$ | 80 | 159 | 13.4 | 34.4 | 39.1 | 8.6 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| | ToS = 24-48 hrs | | | | |
| ~9.3 g Ga/100 g $ZrO_2$ | 0.81 | 3.7 | 1.7 | 1.0 | 48.0 |
| ~3.3 g Ga/100 g $ZrO_2$ | 0.81 | 2.3 | 1.8 | 0.9 | 48.8 |
| | ToS = 72-96 hrs | | | | |
| ~9.3 g Ga/100 g $ZrO_2$ | 0.81 | 4.0 | 1.7 | 0.8 | 48.4 |
| ~3.3 g Ga/100 g $ZrO_2$ | 0.82 | 2.5 | 1.9 | 0.8 | 49.0 |

Table 3b shows the results a process for converting syngas into olefins with the following process conditions: syngas process $H_2/CO$ approximately 3; temperature of 420° C.; pressure of 40 bar; and GHSV equals 2400/h.

TABLE 3b

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~9.3 g Ga/100 g $ZrO_2$ | 130 | 234 | 14.9 | 72.5 | 20.5 | 33.9 |
| ~1.7 g Ga and ~1.9 g Zn/100 g $ZrO_2$ | 125 | 225 | 13.6 | 78.7 | 17.3 | 36.7 |
| ~3.3 g Ga/100 g $ZrO_2$ | 127 | 220 | 19.3 | 74.7 | 25.8 | 29.1 |
| ToS = 72-96 hrs | | | | | | |
| ~9.3g Ga/100 g $ZrO_2$ | 130 | 234 | 14.7 | 71.7 | 20.5 | 33.7 |
| ~1.7 g Ga and ~1.9 g Zn/100 g $ZrO_2$ | 125 | 225 | 9.8 | 78.0 | 12.5 | 40.9 |
| ~3.3 g Ga/100 g $ZrO_2$ | 127 | 220 | 18.8 | 74.5 | 25.2 | 29.8 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs | | | | | |
| ~9.3 g Ga/100 g $ZrO_2$ | 0.38 | 1.4 | 5.4 | 3.2 | 35.6 |
| ~1.7 g Ga and ~1.9 g Zn/100 g $ZrO_2$ | 0.32 | 2.4 | 4.9 | 4.0 | 34.6 |
| ~3.3 g Ga/100 g $ZrO_2$ | 0.47 | 1.4 | 5.7 | 2.6 | 35.3 |
| ToS = 72-96 hrs | | | | | |
| ~9.3 g Ga/100 g $ZrO_2$ | 0.38 | 1.6 | 5.3 | 3.3 | 35.6 |
| ~1.7 g Ga and ~1.9 g Zn/100 g $ZrO_2$ | 0.23 | 3.0 | 4.1 | 5.0 | 34.5 |
| ~3.3 g Ga/100 g $ZrO_2$ | 0.46 | 1.6 | 5.7 | 2.8 | 35.0 |

Example 1 demonstrates that Ga—$ZrO_2$ microporous prepared in various loadings deposited on monoclinic zirconia and tested with SAPO-34 as the microporous catalyst component under varied conditions of feeds ($H_2$/CO approximately 2 or approximately 3) and process (temperature and pressure). This example shows the effectiveness of lower loadings of Ga as well as the effectiveness of a zirconia support in the metal oxide catalyst component.

Example 2

This example included catalysts with SAPO-34 as the microporous catalyst component and featuring $ZrO_2$-supported gallium as the metal oxide catalyst component (monoclinic-$ZrO_2$, BET surface area approximately 100 m$^2$/g) using an impregnation approach. The amounts of the sized 60-80 mesh mixed oxide particles used to prepare hybrid catalyst beds are reported in the Table 4a and 4b. Hybrid catalysts were prepared upon gentle shaking of particles together in a vial.

Table 4a shows the results a process for converting syngas into olefins with the following process conditions $H_2$/CO approximately 2; temperature of 390° C.; pressure of 20 bar (2,000 kPa); and GHSV equals 1200/h.

TABLE 4a

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~0.3 g Ga/100 g $ZrO_2$ | 80 | 159 | 10.8 | 28.4 | 38.0 | 7.8 |
| ~0.6 g Ga/100 g | 81 | 157 | 14.4 | 36.3 | 39.7 | 7.0 |

TABLE 4a-continued

| | | | | | | |
|---|---|---|---|---|---|---|
| ZrO$_2$ | | | | | | |
| ~1.1 g Ga/100 g ZrO$_2$ | 82 | 155 | 15.3 | 39.2 | 39.1 | 7.5 |
| ~2.2 g Ga/100 g ZrO$_2$ | 84 | 151 | 16.8 | 41.1 | 40.9 | 6.4 |
| ToS = 72-96 hrs | | | | | | |
| ~0.3 g Ga/100 g ZrO$_2$ | 80 | 159 | 10.5 | 27.3 | 38.4 | 7.0 |
| ~0.6 g Ga/100 g ZrO$_2$ | 81 | 157 | 13.3 | 33.3 | 40.1 | 6.3 |
| ~1.1 g Ga/100 g ZrO$_2$ | 82 | 155 | 14.0 | 36.3 | 38.5 | 7.1 |
| ~2.2 g Ga/100 g ZrO$_2$ | 84 | 151 | 15.1 | 37.5 | 40.2 | 6.3 |

| Oxide component present in admixture with SAPO-34 | Olefin Fraction in [C$_2$-C$_3$ Product] | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|---|
| ToS = 24-48 hrs | | | | | |
| ~0.3 g Ga/100 g ZrO$_2$ | 0.83 | 3.9 | 2.6 | 0.7 | 48.8 |
| ~0.6 g Ga/100 g ZrO$_2$ | 0.85 | 1.5 | 2.9 | 0.6 | 50.0 |
| ~1.1 g Ga/100 g ZrO$_2$ | 0.84 | 2.4 | 2.7 | 0.8 | 49.3 |
| ~2.2 g Ga/100 g ZrO$_2$ | 0.86 | 1.4 | 2.7 | 0.8 | 49.6 |
| ToS = 72-96 hrs | | | | | |
| ~0.3 g Ga/100 g ZrO$_2$ | 0.85 | 4.1 | 2.8 | 0.6 | 48.5 |
| ~0.6 g Ga/100 g ZrO$_2$ | 0.86 | 1.6 | 3.3 | 0.8 | 49.5 |
| ~1.1 g Ga/100 g ZrO$_2$ | 0.84 | 2.9 | 2.9 | 0.8 | 49.5 |
| ~2.2 g Ga/100 g ZrO$_2$ | 0.86 | 1.6 | 2.8 | 0.7 | 50.1 |

Table 4b shows the results a process for converting syngas into olefins with the following process conditions: H$_2$/CO approximately 3; temperature of 420° C.; pressure of 40 bar (4,000 kPa); and GHSV equals 2400/h.

TABLE 4b

| Oxide component present in admixture with SAPO-34 | SAPO-34 Weight (mg) | Oxide Weight (mg) | Yield C$_2$-C$_3$ Olefins [C mol %] | CO Conv. [C mol. %] | Selectivity C$_2$-C$_3$ Olefin [C mol %] | Selectivity C$_2$-C$_3$ Paraffin [C mol %] |
|---|---|---|---|---|---|---|
| ToS = 24-48 hrs | | | | | | |
| ~0.3 g Ga/100 g ZrO$_2$ | 106 | 225 | 21.8 | 52.4 | 41.6 | 13.3 |
| ~0.6 g Ga/100 g ZrO$_2$ | 101 | 221 | 24.3 | 60.9 | 39.8 | 15.5 |
| ~3.1 g Ga/100 g ZrO$_2$ | 130 | 170 | 20.9 | 76.9 | 27.2 | 27.9 |
| ToS = 72-96 hrs | | | | | | |
| ~0.3 g Ga/100 g ZrO$_2$ | 106 | 225 | 21.4 | 52.0 | 41.1 | 13.8 |
| ~0.6 g Ga/100 g ZrO$_2$ | 101 | 221 | 23.6 | 60.5 | 38.9 | 16.3 |
| ~3.1 g Ga/100 g ZrO$_2$ | 130 | 170 | 20.3 | 75.6 | 26.9 | 28.1 |

| Oxide component present in admixture with SAPO-34 | Olefin Fraction in [C$_2$-C$_3$ Product] | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|---|

TABLE 4b-continued

| | | ToS = 24-48 hrs | | | | |
|---|---|---|---|---|---|---|
| ~0.3 g Ga/100 g ZrO$_2$ | 0.76 | 1.1 | 3.8 | 1.3 | 38.9 | |
| ~0.6 g Ga/100 g ZrO$_2$ | 0.72 | 1.1 | 4.0 | 1.4 | 38.2 | |
| ~3.1 g Ga/100 g ZrO$_2$ | 0.49 | 1.2 | 5.7 | 2.5 | 35.6 | |
| | | ToS = 72-96 hrs | | | | |
| ~0.3 g Ga/100 g ZrO$_2$ | 0.75 | 1.2 | 3.8 | 1.3 | 38.9 | |
| ~0.6 g Ga/100 g ZrO$_2$ | 0.70 | 1.1 | 3.9 | 1.4 | 38.3 | |
| ~3.1 g Ga/100 g ZrO$_2$ | 0.49 | 1.3 | 5.6 | 2.6 | 35.5 | |

Example 2 further demonstrates that Ga-deposited on monoclinic zirconia enables very high olefin yields of composite catalysts in various syngas feeds (2, 3) and process conditions. Very low loadings of Ga can enable an active material for monoclinic ZrO$_2$ of a high surface area.

Example 3

This example included composite catalysts with SAPO-34 as the microporous catalyst component and featuring ZrO$_2$-supported gallium catalysts (tetragonal-ZrO$_2$, BET surface area approximately 130 m$^2$/g). The amounts of the sized 60-80 mesh mixed oxide particles used to prepare hybrid catalyst beds are reported in the Table 5a and 5b. Hybrid catalysts were prepared upon gentle shaking of particles together in a vial.

Table 5a shows the results a process for converting syngas into olefins with the following process conditions: H$_2$/CO approximately 2; temperature 390° C.; pressure 20 bar (2,000 kPa); and GHSV equals 1200/h.

TABLE 5a

| Oxide component present in admixture with SAPO-34 | SAPO-34 Weight (mg) | Oxide Weight (mg) | Yield C$_2$-C$_3$ Olefins [C mol %] | CO Conv. [C mol. %] | Selectivity C$_2$-C$_3$ Olefin [C mol %] | Selectivity C$_2$-C$_3$ Paraffin [C mol %] |
|---|---|---|---|---|---|---|
| | | ToS = 24-48 hrs | | | | |
| ~0.3 g Ga/100 g ZrO$_2$ | 80 | 155 | 4.7 | 13.5 | 34.7 | 11.2 |
| ~0.6 g Ga/100 g ZrO$_2$ | 80 | 153 | 7.1 | 17.0 | 41.8 | 8.7 |
| ~1.1 g Ga/100 g ZrO$_2$ | 81 | 159 | 9.8 | 23.1 | 42.5 | 8.0 |
| ~2.2 g Ga/100 g ZrO$_2$ | 84 | 159 | 11.1 | 26.0 | 42.6 | 9.3 |
| | | ToS = 72-96 hrs | | | | |
| ~0.3 g Ga/100 g ZrO$_2$ | 80 | 155 | 4.5 | 12.4 | 36.8 | 10.2 |
| ~0.6 g Ga/100 g ZrO$_2$ | 80 | 153 | 6.7 | 15.9 | 42.3 | 8.2 |
| ~1.1 g Ga/100 g ZrO$_2$ | 81 | 159 | 9.3 | 21.8 | 42.5 | 7.7 |
| ~2.2 g Ga/100 g ZrO$_2$ | 84 | 159 | 10.9 | 25.2 | 43.3 | 8.7 |

| Oxide component present in admixture with SAPO-34 | Olefin Fraction in [C$_2$-C$_3$ Product] | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|---|
| | ToS = 24-48 hrs | | | | |
| ~0.3 g Ga/100 g ZrO$_2$ | 0.75 | 7.2 | 1.8 | 0.7 | 45.3 |
| ~0.6 g Ga/100 g ZrO$_2$ | 0.83 | 3.1 | 2.1 | 0.6 | 45.2 |
| ~1.1 g Ga/100 g ZrO$_2$ | 0.84 | 2.9 | 2.0 | 0.7 | 45.4 |
| ~2.2 g Ga/100 g ZrO$_2$ | 0.82 | 2.3 | 2.0 | 0.8 | 45.0 |
| | ToS = 72-96 hrs | | | | |

TABLE 5a-continued

| | | | | | |
|---|---|---|---|---|---|
| ~0.3 g Ga/100 g ZrO$_2$ | 0.78 | 7.1 | 1.5 | 0.6 | 44.4 |
| ~0.6 g Ga/100 g ZrO$_2$ | 0.84 | 3.5 | 1.7 | 0.6 | 45.3 |
| ~1.1 g Ga/100 g ZrO$_2$ | 0.85 | 3.3 | 2.0 | 0.7 | 45.1 |
| ~2.2 g Ga/100 g ZrO$_2$ | 0.83 | 2.6 | 1.8 | 0.7 | 45.2 |

Table 5b shows the results a process for converting syngas into olefins with the following process conditions: H$_2$/CO approximately 3; temperature of 420° C.; pressure of 40 bar (4,000 kPa); and GHSV equals 2400/h.

TABLE 5b

| Oxide component present in admixture with SAPO-34 | SAPO-34 Weight (mg) | Oxide Weight (mg) | Yield C$_2$-C$_3$ Olefins [C mol %] | CO Conv. [C mol. %] | Selectivity C$_2$-C$_3$ Olefin [C mol %] | Selectivity C$_2$-C$_3$ Paraffin [C mol %] |
|---|---|---|---|---|---|---|
| ToS = 24-48 hrs | | | | | | |
| ~0.3 g Ga/100 g ZrO$_2$ | 100 | 226 | 7.6 | 19.6 | 38.6 | 24.0 |
| ~0.6 g Ga/100 g ZrO$_2$ | 106 | 239 | 11.8 | 28.4 | 41.6 | 19.4 |
| ~1.1 g Ga/100 g ZrO$_2$ | 109 | 208 | 14.2 | 35.7 | 39.7 | 21.0 |
| ~2.2 g Ga/100 g ZrO$_2$ | 105 | 236 | 18.6 | 46.5 | 40.1 | 19.5 |
| ToS = 72-96 hrs | | | | | | |
| ~0.3 g Ga/100 g ZrO$_2$ | 100 | 226 | 6.7 | 17.9 | 37.4 | 26.5 |
| ~0.6 g Ga/100 g ZrO$_2$ | 106 | 239 | 10.4 | 25.7 | 40.5 | 21.6 |
| ~1.1 g Ga/100 g ZrO$_2$ | 109 | 208 | 12.6 | 32.8 | 38.6 | 23.1 |
| ~2.2 g Ga/100 g ZrO$_2$ | 105 | 236 | 17.1 | 43.6 | 39.1 | 21.1 |

| Oxide component present in admixture with SAPO-34 | Olefin Fraction in [C$_2$-C$_3$ Product] | Selectivity CH$_4$ [C mol %] | Selectivity C$_4$ Olefins [C mol %] | Selectivity C$_4$-C$_5$ Paraffins [C mol %] | Selectivity CO$_2$ [C mol %] |
|---|---|---|---|---|---|
| ToS = 24-48 hrs | | | | | |
| ~0.3 g Ga/100 g ZrO$_2$ | 0.62 | 1.5 | 3.8 | 1.5 | 30.6 |
| ~0.6 g Ga/100 g ZrO$_2$ | 0.68 | 1.3 | 3.6 | 1.4 | 32.7 |
| ~1.1 g Ga/100 g ZrO$_2$ | 0.65 | 1.3 | 3.6 | 1.5 | 33.1 |
| ~2.2 g Ga/100 g ZrO$_2$ | 0.67 | 1.2 | 3.8 | 1.5 | 33.7 |
| ToS = 72-96 hrs | | | | | |
| ~0.3 g Ga/100 g ZrO$_2$ | 0.59 | 1.6 | 3.7 | 1.5 | 29.4 |
| ~0.6 g Ga/100 g ZrO$_2$ | 0.65 | 1.4 | 3.5 | 1.5 | 31.5 |
| ~1.1 g Ga/100 g ZrO$_2$ | 0.63 | 1.3 | 3.4 | 1.5 | 32.1 |
| ~2.2 g Ga/100 g ZrO$_2$ | 0.65 | 1.3 | 3.7 | 1.6 | 33.1 |

This example demonstrated that Ga-deposited on tetragonal zirconia is an active component to catalyst composite (dual-particle bed). However, overall performance is inferior to Ga—ZrO$_2$ prepared on monoclinic-ZrO$_2$ as for operations presented in Example 2.

Example 4

This example included hybrid catalysts featuring ZrO$_2$-supported gallium metal oxide catalyst components that also comprise other elements either in the zirconia carrier and/or co-impregnated with the gallium precursor. In the first instance (Table 6a), zirconia carrier was identified as tetragonal zirconia that contained some lanthanum (La) (NORPRO, product no. SZ61156, containing approximately 7.3 g La per 100 g ZrO$_2$). Gallium was impregnated onto this support either alone or co-impregnated with an additional amount of lanthanum. The latter case is evidenced with an increased amount of La in the sample (the first vs the second entry in the table). The amounts of the sized 60-80 mesh mixed oxide particles used to prepare hybrid catalyst beds are reported in the Table 6a. Hybrid catalysts were prepared upon gentle shaking of particles together in a vial.

Table 6a shows the results a process for converting syngas into olefins with the following process conditions: $H_2/CO=3$; temperature of 390° C.; pressure 30 bar; and GHSV equals 1200/h.

TABLE 6a

| Oxide component present in admixture with SAPO-34 | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs ||||||||
| ~1.2 g Ga and ~7.3 g La/100 g $ZrO_2$ | 74 | 159 | 15.5 | 47.3 | 33.2 | 10.7 |
| ~1.2 g Ga and ~8.6 g La/100 g $ZrO_2$ | 74 | 166 | 16.3 | 45.8 | 36.1 | 10.2 |
| ToS = 72-96 hrs ||||||||
| ~1.2 g Ga and ~7.3 g La/100 g $ZrO_2$ | 74 | 159 | 13.8 | 43.3 | 32.3 | 10.6 |
| ~1.2 g Ga and ~8.6 g La/100 g $ZrO_2$ | 74 | 166 | 15.4 | 43.7 | 35.9 | 9.9 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs ||||||
| ~1.2 g Ga and ~7.3 g La/100 g $ZrO_2$ | 0.76 | 2.8 | 7.9 | 1.3 | 45.2 |
| ~1.2 g Ga and ~8.6 g La/100 g $ZrO_2$ | 0.78 | 2.7 | 7.4 | 1.1 | 44.2 |
| ToS = 72-96 hrs ||||||
| ~1.2 g Ga and ~7.3 g La/100 g $ZrO_2$ | 0.75 | 3.6 | 7.9 | 1.0 | 45.8 |
| ~1.2 g Ga and ~8.6 g La/100 g $ZrO_2$ | 0.78 | 3.1 | 7.3 | 1.0 | 44.5 |

Table 6b shows the results a process for converting carbon oxide and carbon dioxide (COx Conversion) into olefins with the following process conditions: $H_2/CO/CO_2$ equals 69.1/13.6/6.9 vol %; temperature of 390° C.; pressure 30 bar, GHSV equals 1200/h. Along the catalytic materials referenced in the Table 6a, the test further included additional samples prepared on zirconia carrier identified as tetragonal zirconia that contained some tungsten (W) (NORPRO, product no. SZ61143, contains approximately 11 wt % W). Ga-precursor was impregnated onto this support either alone or co-impregnated with La-precursor (third vs fourth entry in the Table 6b).

TABLE 6b

| Oxide component present in admixture with SAPO-34 | SAPO-34 Weight (mg) | Oxide Weight (mg) | Yield $C_2$-$C_3$ Olefins [C mol %] | COx Conv. [C mol. %] | Selectivity $C_2$-$C_3$ Olefin [C mol %] | Selectivity $C_2$-$C_3$ Paraffin [C mol %] |
|---|---|---|---|---|---|---|
| ToS = 24-48 hrs | | | | | | |
| ~1.2 g Ga and ~7.3 g La/100 g $ZrO_2$ | 92 | 135 | 8.76 | 14.65 | 59.82 | 24.91 |
| ~1.2 g Ga and ~8.6 g La/100 g $ZrO_2$ | 92 | 135 | 8.61 | 14.88 | 57.95 | 28.42 |
| ~1.3 g Ga and ~13.6 g W/100 g $ZrO_2$ | 87 | 152 | 1.07 | 8.28 | 13.07 | 30.35 |
| ~1.2 g Ga and ~1.2 g La and 13.6 g W/100 g $ZrO_2$ | 90 | 156 | 0.87 | 8.46 | 10.19 | 53.92 |
| ToS = 72-96 hrs | | | | | | |
| ~1.2 g Ga and ~7.3 g La/100 g $ZrO_2$ | 92 | 135 | 8.62 | 14.03 | 61.42 | 22.32 |
| ~1.2 g Ga and ~8.6 g La/100 g $ZrO_2$ | 92 | 135 | 8.62 | 14.33 | 60.35 | 25.32 |
| ~1.3 g Ga and ~13.6 g W/100 g $ZrO_2$ | 87 | 152 | 0.98 | 8.09 | 12.24 | 27.76 |
| ~1.2 g Ga and ~1.2 g La and 13.6 g W/100 g $ZrO_2$ | 90 | 156 | 0.97 | 8.02 | 12.01 | 48.96 |

| | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] |
|---|---|---|---|---|
| ToS = 24-48 hrs | | | | |
| ~1.2 g Ga and ~7.3 g La/100 g $ZrO_2$ | 0.71 | 9.39 | 4.05 | 1.83 |
| ~1.2 g Ga and ~8.6 g La/100 g $ZrO_2$ | 0.67 | 7.63 | 4.17 | 1.82 |
| ~1.3 g Ga and ~13.6 g W/100 g $ZrO_2$ | 0.3 | 53.65 | 0.17 | 2.75 |
| ~1.2 g Ga and ~1.2 g La and 13.6 g W/100 g $ZrO_2$ | 0.16 | 25.42 | 2.1 | 8.36 |
| ToS = 72-96 hrs | | | | |
| ~1.2 g Ga and ~7.3 g La/100 g $ZrO_2$ | 0.73 | 10.72 | 3.74 | 1.79 |
| ~1.2 g Ga and ~8.6 g La/100 g $ZrO_2$ | 0.7 | 8.47 | 3.5 | 2.35 |
| ~1.3 g Ga and ~13.6 g W/100 g $ZrO_2$ | 0.31 | 57.55 | 0 | 2.46 |
| ~1.2 g Ga and ~1.2 g La and 13.6 g W/100 g $ZrO_2$ | 0.2 | 28.8 | 2.12 | 8.11 |

Example 4 demonstrates that Ga-deposited on tetragonal zirconia with La in the support is an active and stable composite catalyst. In contrast, tetragonal zirconia with W present significantly impairs its catalytic behavior. Co-impregnated La can mitigate some adverse effects of W-present (i.e., an effect on methane selectivity).

Example 5

This example included catalysts with SAPO-34 microporous catalyst components and featuring $ZrO_2$-supported gallium/lanthanum catalyst. As carrier to prepare the latter a commercial sample of monoclinic-$ZrO_2$ was used (NOR- PRO product no. SZ31108, BET surface area approximately 70 m²/g). The catalyst was tested in a long process run across varied process conditions.

Table 7a shows the results for converting syngas into olefins for one hybrid catalyst in a process study during which process conditions were changed in time of the process. The hybrid catalyst was prepared from 123 mg of SAPO-34 component and 185 mg of the mixed Ga—La/$ZrO_2$ mixed oxide component upon gentle shaking of sized particles 60-80 mesh of both components together in a vial. The average catalytic results are reported for each process segment and include start and finish of each process segment (Min ToS [hrs]–Max ToS [hrs]) Note, that time-on-stream was counted from the onset of the exposure to syngas. Each process segment had different process operations parameters like $H_2$/CO ratio and space velocity while, the temperature and pressure of the process were kept constant.

60-80 mesh of both components together in a vial. The average catalytic results are reported for each process segment and include start and finish of each process segment (Min ToS [hrs]–Max ToS [hrs]) Note, that time-on-stream was counted from the onset of the exposure to syngas. Each process segment had different process operations parameters like $H_2$/CO ratio, space velocity or temperature, while pressure of the process was kept constant (30 bars).

TABLE 7a

| Oxide component present in admixture with SAPO-34 | SAPO-34 Weight (mg) | Oxide Weight (mg) | Min ToS [hrs] | Max ToS [hrs] | SYNGAS | SP GHSV [h−1] | P [bar] | T [° C.] |
|---|---|---|---|---|---|---|---|---|
| ~2.2 g Ga and 1.45 g La/100 g $ZrO_2$ | 123 | 185 | 108.1 | 143.9 | 2.9 | 1800.0 | 40.0 | 400.0 |
|  |  |  | 146.6 | 184.5 | 2.9 | 2400.0 | 40.0 | 400.0 |
|  |  |  | 187.3 | 225.3 | 3.2 | 1200.0 | 40.0 | 400.0 |

| Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|---|---|---|
| 20.8 | 66.6 | 31.3 | 20.6 | 0.60 | 1.1 | 8.8 | 2.4 | 35.8 |
| 19.9 | 59.7 | 33.4 | 18.1 | 0.65 | 1.1 | 8.4 | 2.3 | 36.8 |
| 18.7 | 75.1 | 25.0 | 27.6 | 0.47 | 1.2 | 9.4 | 2.8 | 34.0 |

Table 7b shows the results a process for converting syngas into olefins with the following process conditions: $H_2$/CO TABLE 7b

| Oxide component present in admixture with SAPO-34 | SAPO-34 Weight (mg) | Oxide Weight (mg) | Min ToS [hrs] | Max ToS [hrs] | SYNGAS | SP GHSV [h⁻¹] | P [bar] | T [° C.] |
|---|---|---|---|---|---|---|---|---|
| ~2.2 g Ga and 1.45 g La/100 g $ZrO_2$ | 147 | 130 | 110.7 | 163.8 | 3.0 | 1800.0 | 30.0 | 390.0 |
|  |  |  | 166.9 | 220.0 | 3.0 | 2400.0 | 30.0 | 390.0 |
|  |  |  | 223.1 | 276.4 | 3.3 | 1200.0 | 30.0 | 390.0 |
|  |  |  | 279.5 | 298.5 | 3.3 | 1200.0 | 30.0 | 395.0 |
|  |  |  | 301.6 | 326.0 | 3.3 | 1200.0 | 30.0 | 400.0 |

| Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|---|---|---|
| 18.5 | 47.7 | 38.7 | 16.5 | 0.70 | 1.0 | 4.8 | 1.7 | 37.2 |
| 16.4 | 42.5 | 38.7 | 15.6 | 0.71 | 1.1 | 4.8 | 1.7 | 37.8 |
| 20.2 | 56.8 | 35.5 | 20.1 | 0.64 | 1.0 | 5.4 | 1.8 | 36.1 |
| 21.0 | 59.7 | 35.2 | 20.8 | 0.63 | 1.0 | 5.3 | 1.7 | 35.9 |
| 21.1 | 62.7 | 33.6 | 22.9 | 0.59 | 1.1 | 5.4 | 1.8 | 35.3 | approximately 3; temperature of 390 to 400° C.; pressure equals 30 bar; and GHSV equals 1200/h to 2400/h.

Table 7b shows the results for converting syngas into olefins for hybrid catalyst in a long process study where process conditions were changed in time of the process. The hybrid catalyst was prepared from 147 mg of SAPO-34 component and 130 mg of the mixed Ga—La/$ZrO_2$ mixed oxide component upon gentle shaking of sized Example 5 demonstrates that Ga/La—$ZrO_2$ can sustain syngas to olefin process over prolonged times and in high yield in olefins across various process (p, T, GHSV) conditions.

Example 6

This example included hybrid catalysts with SAPO-34 microporous catalyst components featuring Ga—$ZrO_2$ metal oxide catalyst component. It compares a semi-crystalline co-precipitated mixed oxide Ga—$ZrO_2$ (a synthetic methodology alternative to impregnation) where an intimate junction-Ga—$ZrO_2$ may exist but $ZrO_2$ shows poor crystallinity effectively rendering an inferior catalytic system. It also compares Ga—$ZrO_2$ prepared via slurry-processing & calcination of crystalline monoclinic-$ZrO_2$ and a Ga-precursor in a form of $Ga_2O_3$ (a synthetic methodology alternative to impregnation) where crystalline powders produce the desired catalytic effect. Furthermore it compares to a physical mixture of powders without any processing to create an intimate junction of $Ga_2O_3$ and $ZrO_2$ where the hybrid system with SAPO-34 shows an underdeveloped catalytic performance. The amounts of the sized 60-80 mesh mixed oxide particles used to prepare hybrid catalyst beds are reported in the Table 8a. Hybrid catalysts were prepared upon gentle shaking of particles together in a vial.

Table 8a shows the results a process for converting syngas into olefins with the following process conditions: $H_2$/CO approximately 3; temperature of 420° C.; pressure equals 40 bar (4,000 kPa); and GHSV equals 2400/h.

TABLE 8a

| Oxide component present in admixture with SAPO-34 | Preparation/ comments | SAPO-34 Weight (mg) | Oxide Weight (mg) | Yield $C_2$-$C_3$ Olefins [C mol %] | CO Conv. [C mol. %] | Selectivity $C_2$-$C_3$ Olefin [C mol %] | Selectivity $C_2$-$C_3$ Paraffin [C mol %] |
|---|---|---|---|---|---|---|---|
| ToS = 24-48 hrs | | | | | | | |
| ~13.2 g Ga/100 g $ZrO_2$ | Co-precipitation/ lacks crystalline $ZrO_2$ | 111 | 78 | 1.3 | 16.8 | 7.5 | 36.5 |
| ~1.7 g Ga/100 g $ZrO_2$ | slurry-processing/ crystalline $ZrO_2$ | 102 | 181 | 15.4 | 40.0 | 38.6 | 17.9 |
| ~14.0 g Ga/100 g $ZrO_2$ | Slurry-processing/ crystalline $ZrO_2$ | 99 | 180 | 19.5 | 51.7 | 37.7 | 18.5 |
| ~41.7 g Ga/100 g $ZrO_2$ | Slurry-processing/ crystalline $ZrO_2$ | 104 | 181 | 12.8 | 47.0 | 27.3 | 28.5 |
| ~2.72 g Ga/100 g $ZrO_2$ | dry powder mix/ crystalline $ZrO_2$ | 99 | 181 | 6.1 | 25.4 | 23.9 | 29.2 |
| ~20.4 g Ga/100 g $ZrO_2$ | dry powder mix/ crystalline $ZrO_2$ | 103 | 187 | 9.0 | 36.3 | 24.9 | 29.3 |
| ToS = 72-96 hrs | | | | | | | |
| ~13.2 g Ga/100 g $ZrO_2$ | Co-precipitation/ lacks crystalline $ZrO_2$ | 111 | 78 | 1.2 | 14.7 | 8.4 | 34.3 |
| ~1.7 g Ga/100 g $ZrO_2$ | slurry-processing/ crystalline $ZrO_2$ | 102 | 181 | 15.5 | 40.8 | 37.9 | 18.3 |
| ~14.0 g Ga/100 g $ZrO_2$ | Slurry-processing/ crystalline $ZrO_2$ | 99 | 180 | 19.3 | 51.5 | 37.5 | 18.3 |
| ~41.7 g Ga/100 g $ZrO_2$ | Slurry-processing/ crystalline $ZrO_2$ | 104 | 181 | 12.2 | 45.6 | 26.8 | 28.6 |
| ~2.72 g Ga/100 g $ZrO_2$ | dry powder mix/ crystalline $ZrO_2$ | 99 | 181 | 6.4 | 27.2 | 23.5 | 29.2 |
| ~20.4 g Ga/100 g $ZrO_2$ | dry powder mix/ crystalline $ZrO_2$ | 103 | 187 | 9.0 | 36.7 | 24.5 | 29.4 |

| Oxide component present in admixture with SAPO-34 | Olefin Fraction in [$C_2$-$C_3$ Product] | Selectivity $CH_4$ [C mol %] | Selectivity $C_4$ Olefins [C mol %] | Selectivity $C_4$-$C_5$ Paraffins [C mol %] | Selectivity $CO_2$ [C mol %] |
|---|---|---|---|---|---|
| ToS = 24-48 hrs | | | | | |
| ~13.2 g Ga/100 g $ZrO_2$ | 0.17 | 6.5 | 1.4 | 8.3 | 39.5 |
| ~1.7 g Ga/100 g $ZrO_2$ | 0.68 | 1.3 | 1.8 | 1.5 | 39.0 |
| ~14.0 g Ga/100 g $ZrO_2$ | 0.67 | 1.6 | 1.7 | 2.2 | 38.2 |
| ~41.7 g Ga/100 g $ZrO_2$ | 0.49 | 1.9 | 1.6 | 3.2 | 37.6 |
| ~2.72 g Ga/100 g $ZrO_2$ | 0.45 | 2.6 | 1.7 | 2.4 | 40.2 |
| ~20.4 g Ga/100 g $ZrO_2$ | 0.46 | 2.3 | 1.8 | 2.8 | 38.9 |
| ToS = 72-96 hrs | | | | | |
| ~13.2 g Ga/100 g $ZrO_2$ | 0.20 | 8.3 | 1.4 | 8.0 | 39.6 |
| ~1.7 g Ga/100 g $ZrO_2$ | 0.67 | 1.4 | 1.8 | 1.5 | 39.1 |
| ~14.0 g Ga/100 g $ZrO_2$ | 0.67 | 1.8 | 1.7 | 2.3 | 38.3 |
| ~41.7 g Ga/100 g $ZrO_2$ | 0.48 | 2.1 | 1.6 | 3.3 | 37.6 |
| ~2.72 g Ga/100 g $ZrO_2$ | 0.45 | 2.8 | 1.8 | 2.6 | 40.1 |

TABLE 8a-continued

| | | | | | |
|---|---|---|---|---|---|
| $ZrO_2$ ~20.4 g Ga/100 g $ZrO_2$ | 0.45 | 2.5 | 1.8 | 2.8 | 38.9 |

Example 6 demonstrated that Ga—$ZrO_2$ can be created with different technologies of preparation; however, care must be taken to ensure $ZrO_2$ is delivered in a well crystalline form such as monoclinic polymorph. Methods for obtaining a very active component Ga—$ZrO_2$ to dual-particle catalyst bed with SAPO-34 appears to be impregnation (Examples 1-5). However, upon certain process operations physical mixtures of $ZrO_2$ and $Ga_2O_3$ may also gain activity with prolonged process exposure affecting re-distribution of elements in presence of reactants and product gases.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ to $C_4$ olefins comprising:
   introducing a feed stream comprising hydrogen gas and a carbon-containing gas selected from the group consisting of carbon monoxide, carbon dioxide, and mixtures thereof into a reaction zone of a reactor; and
   converting the feed stream into a product stream comprising $C_2$ to $C_4$ olefins in the reaction zone in the presence of a hybrid catalyst, the hybrid catalyst comprising:
      a metal oxide catalyst component comprising gallium oxide and phase pure zirconia; and
      a microporous catalyst component.

2. The process of claim 1, wherein the phase pure zirconia comprises crystalline phase pure zirconia.

3. The process of claim 1, wherein the phase pure zirconia comprises monoclinic phase pure zirconia.

4. The process of claim 1, wherein the phase pure zirconia has a BET surface area that is greater than or equal to 40 $m^2/g$.

5. The process of claim 1, wherein the phase pure zirconia has a BET surface area that is greater than or equal to 100 $m^2/g$.

6. The process of claim 1, wherein the metal oxide catalyst component comprises from greater than 0.0 g gallium per 100 g phase pure zirconia to 30.0 g gallium per 100 g of phase pure zirconia.

7. The process of claim 1, wherein the metal oxide catalyst component comprises from greater than 0.0 g gallium per 100 g phase pure zirconia to 15.0 g gallium per 100 g of phase pure zirconia.

8. The process of claim 1, wherein microporous catalyst component comprises an 8 membered ring structure.

9. The process of claim 1, wherein the microporous catalyst component comprises SAPO-34.

10. The process of claim 1, wherein the metal oxide catalyst component comprises from 1.0 wt % to 99.0 wt % of the hybrid catalyst.

11. The process of claim 1, wherein the metal oxide catalyst component comprises from 60.0 wt % to 90.0 wt % of the hybrid catalyst.

12. The process of claim 1, wherein a temperature within the reaction zone during the converting is from 350° C. to 450° C.

13. The process of claim 1, wherein a pressure within the reaction zone during the converting is at least 1 bar (100 kPa).

14. The process of claim 1, wherein a GHSV within the reaction zone during the converting is from 1,200/h to 12,000/h.

15. The process of claim 1, wherein the metal oxide catalyst component is formed by an impregnation method.

16. The process of claim 1, wherein:
   the phase pure zirconia comprises crystalline phase pure zirconia;
   the metal oxide catalyst component comprises from greater than 0.0 g gallium per 100 g phase pure zirconia to 30.0 g gallium per 100 g of phase pure zirconia; and
   the microporous catalyst component comprises SAPO-34.

17. The process of claim 1, wherein:
   a temperature within the reaction zone during the converting is from 350° C. to 450° C.;
   a pressure within the reaction zone during the converting is at least 1 bar (100 kPa); and
   a GHSV within the reaction zone during the converting is from 1,200/h to 12,000/h.

18. The process of claim 1, wherein the phase pure zirconia is a support for the gallium oxide.

* * * * *